United States Patent
Maruyama et al.

[11] Patent Number: 5,597,456
[45] Date of Patent: Jan. 28, 1997

[54] METHOD FOR PRODUCING MEDICAL MATERIALS

[75] Inventors: Tohru Maruyama, Sagamihara; Michio Abe, Ohita-ken; Hiroaki Nomiyama, Sagamihara; Sachiko Okazaki, No. 20-11, Takaido-Higashi, 2-chome, Suginami-ku, Tokyo; Masuhiro Kogoma, No. 843-15, Shimo-Niikura, Wako-shi, Saitama-ken; Makoto Kodama, Tsukuba, all of Japan

[73] Assignees: Hiroshi Kashiwagi; Agency of Industrial Science & Technology; Sachiko Okazaki, all of Tokyo; Masuhiro Kogoma, Wako; Kawasumi Laboratories Inc., Tokyo, all of Japan

[21] Appl. No.: 595,835

[22] Filed: Feb. 2, 1996

Related U.S. Application Data

[63] Continuation of Ser. No. 254,947, Jun. 7, 1994, abandoned.

[30] Foreign Application Priority Data

| Jul. 6, 1993 | [JP] | Japan | 5-160011 |
| Oct. 22, 1993 | [JP] | Japan | 5-286227 |
| Apr. 28, 1994 | [JP] | Japan | 6-111668 |

[51] Int. Cl.$^6$ .............................. B01K 1/00; B05D 3/06
[52] U.S. Cl. .............................. 204/165; 204/164
[58] Field of Search .................... 204/164, 165, 204/168

[56] References Cited

U.S. PATENT DOCUMENTS

| 4,261,806 | 4/1981 | Asai et al. | 204/165 |
| 4,326,532 | 4/1982 | Hammar | 428/411 |
| 4,786,556 | 11/1988 | Hu et al. | 428/412 |
| 4,927,676 | 5/1990 | Williams et al. | 428/36 |
| 5,132,108 | 7/1992 | Narayanan et al. | 427/40 |

FOREIGN PATENT DOCUMENTS

| 61-168365 | 7/1986 | Japan |
| 62-089737 | 4/1987 | Japan |
| 63-027536 | 2/1988 | Japan |

*Primary Examiner*—Kathryn Gorgos
*Assistant Examiner*—Kishor Mayekar
*Attorney, Agent, or Firm*—Michael J. Striker

[57] ABSTRACT

A plastic tube extruded from an extruder is conveyed through a plasma treatment apparatus. The plasma treatment apparatus is equipped with a tubular electrode body having a high-voltage side electrode and a grounded-side electrode disposed on a tubular insulator and a high frequency electric power source connected to the electrodes. When the plastic tube is conveyed through the electrode body with one end of the tube open to the atmosphere, a mixture of a glow discharge-stabilizing gas and a treating gas is fed into the other end of the tube and an alternating-current high-voltage is applied to generate a plasma region at a pressure near to atmospheric pressure in which the tube is treated with a glow discharge plasma. This method allows an interior and/or exterior surface of a plastic tube designed to convey a medical fluid to be continuously treated by a glow discharge plasma at atmospheric pressure to form an anti-thrombotic and blood-compatible film on the surface treated. The resulting surface-treated medical material can be produced at a comparatively low cost and maintains its original bulk material properties.

12 Claims, 14 Drawing Sheets

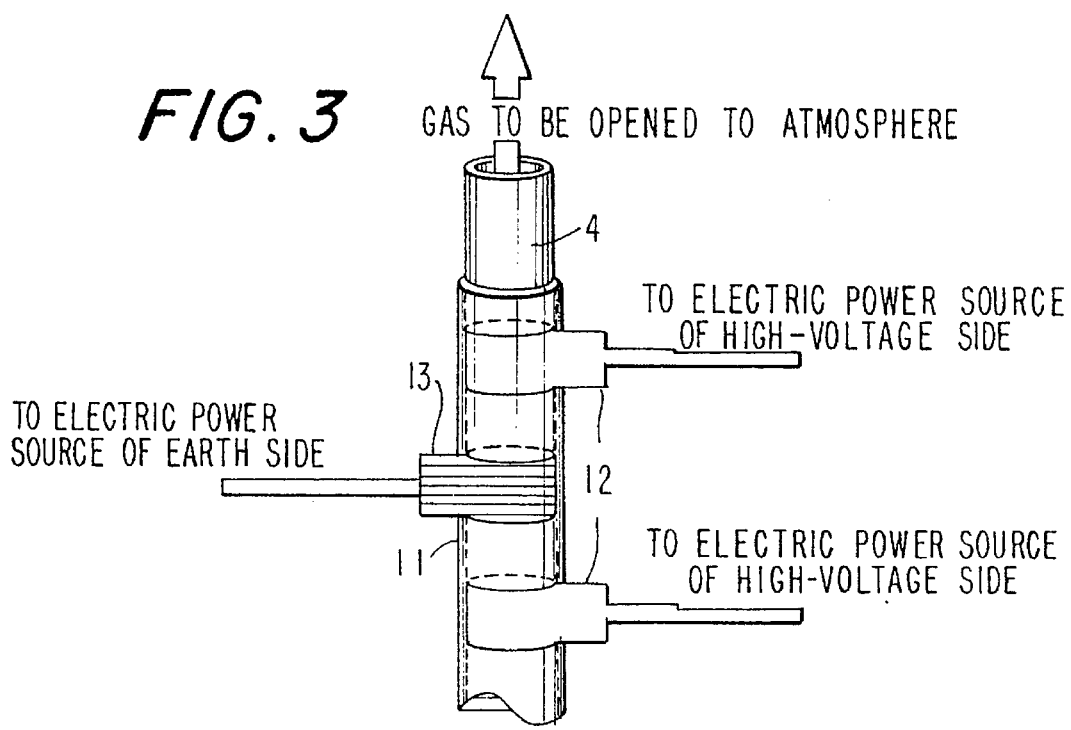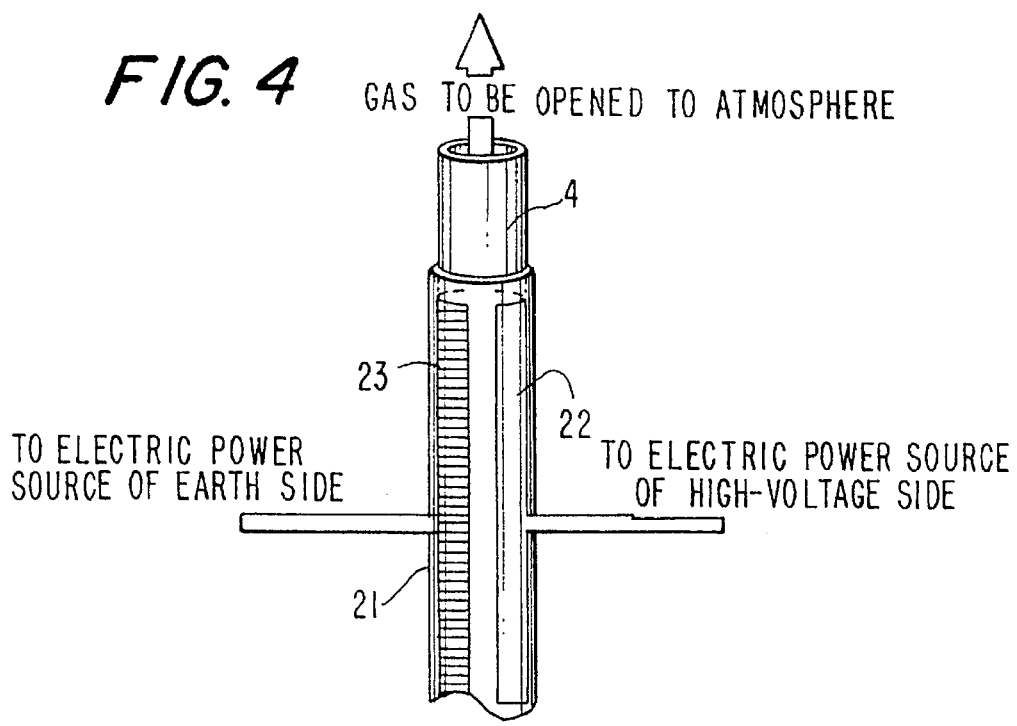

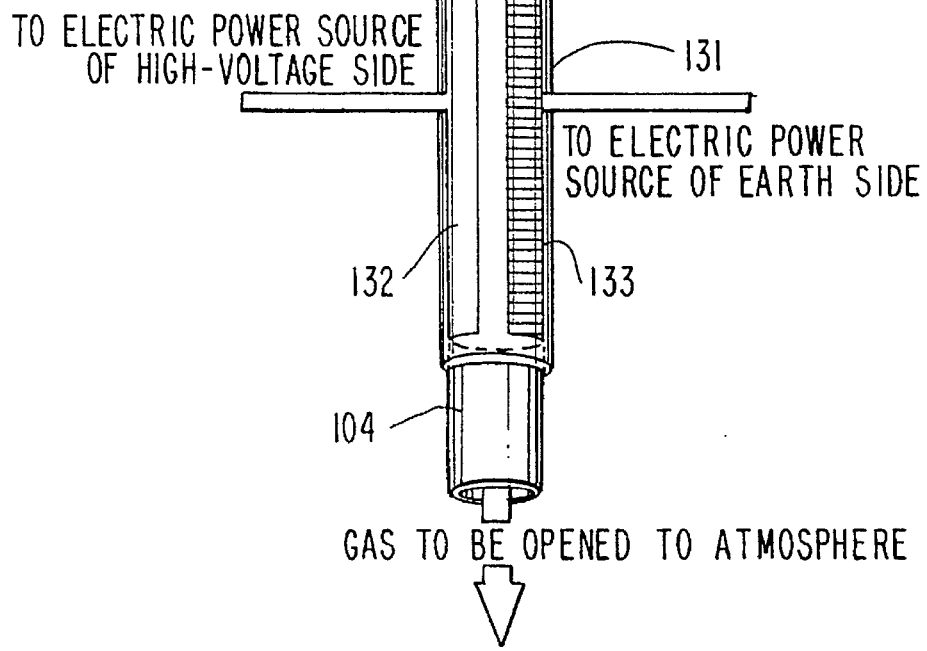
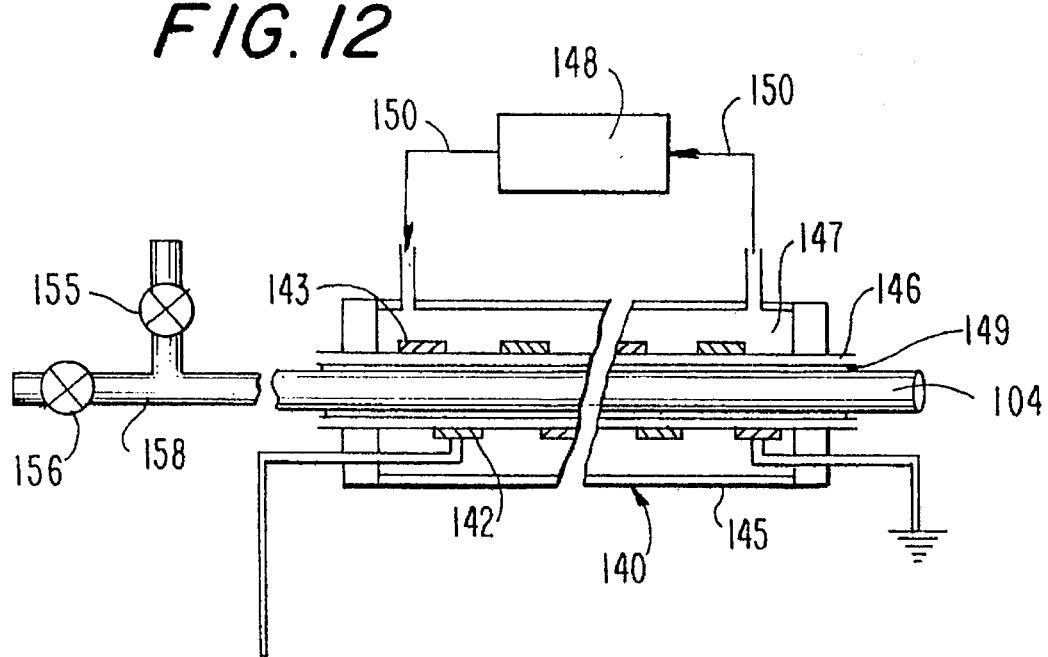

METHOD FOR PRODUCING MEDICAL MATERIALS

This is a continuation of application Ser. No. 08/254,947 filed Jun. 7, 1994 now abandoned.

BACKGROUND OF THE INVENTION

1. Field of the Invention

The present invention relates to anti-thrombotic medical materials and methods for producing them, in which an atmospheric pressure glow discharge plasma treatment is applied to the surface of materials to form films on them. The action of the plasma on the surface produces an anti-thrombotic material.

2. Prior Art

Medical appliances made of plastic materials have been used widely and those used for general purposes include catheters, blood bags, blood transfusion sets, fluid transfusion sets and blood circulating devices for extracorporeal circulation. These appliances are primarily used as disposables and are generally made of thermoplastic materials such as polyethylene, polyethylene terephthalate, poly(vinyl chloride) (PVC), polypropylene and the like. Generally, these materials have excellent mechanical properties, but tend to lack biocompatibility. In particular, it has been found that the blood compatibility of these plastic materials is rather poor because they do not have any effective anti-thrombotic properties.

During past years, therefore, various efforts have been made for the purpose of improving blood compatibility by treating the surface of these macromolecule materials. A material can retain its original mechanical properties after surface treatment. Such efforts have given birth to interesting processes. Japanese Published Patent No. 168365/1986, for example, discloses a process in which a heparin-type anticoagulant is introduced on the surface of synthetic macromolecule materials by ionic bonds or covalent bonds. Another method involving immobilization of a urokinase-type anti-thrombotic agent also exists.

A surface treatment by low-temperature glow discharge plasma has been proposed, in which a blood compatible compound having anti-thrombotic properties is introduced on a treated base material by grafting or chemical vapor deposition (CVD). This glow discharge plasma method is known to be advantageous because only the surface of the material to be treated can be reacted without any pin-holes in the thin films on the surface. During this surface treatment, the physical properties of the bulk material are not made poorer.

In plasma treatment technology, however, currently only corona or arc discharge can occur at atmospheric pressure, but no glow discharge can be easily produced at atmospheric pressure. The glow discharge requires vacuum or reduced pressure. Thus, various modes of operation are used at vacuum conditions to perform the surface treatment continuously. For example, a roll of a material to be treated is set in a vacuum vessel batch-wise, treated with the glow discharge and then withdrawn continuously in the form of a sheet. There is also another method that involves a differential exhaust system, in which the pressure is gradually reduced from atmospheric to a vacuum. Japanese Published Patent No. 27536/1988. discloses this method which uses a sheet of a material in the surface treatment.

These continuous treatment methods, however, require comparatively large volume treatment apparatus as well as a vacuum pump of a great capacity for reducing pressure in the apparatus. Furthermore, fluctuation in the degree of vacuum has a significant effect on the quality of surface treatment so that the vacuum system should be strictly controlled. This makes it physically difficult to install a treatment apparatus of a large size since it must be held under such sensitive vacuum conditions. Other than the additional facilities necessary for establishing a high degree of vacuum, treatment costs may increase to an extent that it may be practically impossible to use this system for producing general-purpose plastic materials. Medical appliances manufactured from these general-purpose materials are often intended to be used as disposables, hence must be comparatively low cost items.

Furthermore, if the material to be treated is in the form of a soft tube, it is very difficult to treat its surface and it is nearly impossible to treat its inner surface, not to mention selective treatment of the surface.

The use of plastic tubes is currently wide spread in various fields. Therefore, the development of simpler, less costly and more widely applicable methods for reforming or treating the surface of plastic tubes is highly desirable.

SUMMARY OF THE INVENTION

It is an object of the present invention to provide novel medical materials and methods for producing the same.

It is another object of the present invention to provide a glow discharge plasma treatment method for materials of any arbitrarily desired shape which is comparatively low-cost, which can be performed at atmospheric pressure without employing vacuum systems and which produces films on the surface of the materials having excellent blood compatibility and anti-thrombotic characteristics while retaining their intrinsic bulk mechanical properties.

It is an additional object of the present invention to provide novel medical materials and methods for producing the same, in which a treating gas which comprises monomers is used to produce films on the surface of the materials having excellent blood compatibility and anti-thrombotic properties.

According to the present invention, an alternating current voltage is applied to a material at a pressure near to atmospheric pressure in the presence of a treatment gas mixture including a glow discharge-stabilizing gas to form an anti-thrombotic film on the treated materials, thus making them suitable for medical uses.

According to one aspect of the invention, the method for conducting the atmospheric pressure glow discharge plasma treatment of the materials comprises the steps of applying the alternating current voltage to a material to be treated at a pressure near to atmospheric pressure so as to form an active ligand on its surface, and then exposing the material to a treating gas, or a mixture of a treating gas and a glow discharge-stabilizing gas, to provide a treated material having anti-thrombotic properties.

According to another aspect of the invention, the atmospheric pressure glow discharge plasma treatment is performed by coating the material to be treated with polymerizable monomers and applying the alternating current voltage to the material to be treated at a pressure near to atmospheric pressure in the presence of a glow discharge-stabilizing gas to provide a treated material having anti-thrombotic properties.

The plasma treatment methods of this invention described herein mean plasma initiation polymerization, plasma CVD, and plasma graft polymerization and any other surface treatment methods performed by means of plasma.

Herein, a pressure near to atmospheric pressure means a pressure obtained in a plasma-forming zone without using any vacuum pump in contrast to the low pressure or vacuum used in low temperature plasma treatments which is produced by a vacuum pump. At the pressure near to atmospheric pressure, any gas in the plasma region is replaced by a mixture of the treating gas and the glow discharge-stabilizing gas, and the gases are continuously fed to the plasma region and discharged from it through a gas outlet that is open to the atmosphere so as to make sure that the plasma region is maintained at a pressure near to atmospheric pressure.

According to this invention, in order to generate the above glow discharge at atmospheric pressure, after the air inside the treating vessel composed of a cylindrical electrode tube and the like has been replaced by a glow discharge-stabilizing gas, or a mixture of the glow discharge-stabilizing gas and the treating gas, or while the glow discharge-stabilizing gas or the mixture of the glow discharge-stabilizing gas and the treating gas, is continuously fed to the treating vessel after the gas has been replaced, the alternating current voltage is applied at a pressure near to atmospheric pressure to generate the plasma. The desired surface-treated materials are obtained from that plasma region.

For example, if the inner surface of a tube is to be treated, then while the mixture of the glow discharge-stabilizing gas and the treating gas is continuously fed into one end of the tube, the tube to be treated is also continuously passed through a cylindrical electrode tube. Then, the alternating current voltage is applied to the cylindrical electrode tube, resulting in formation of a glow discharge plasma, and accordingly the inner surface of the tube is then selectively treated.

Furthermore, if the outer surface of a tube is to be treated, then while the mixture of the glow discharge-stabilizing gas and the treating gas is continuously fed to an annulus between the tube and electrode, the tube to be treated is also continuously passed through the cylindrical electrode tube. Then, the alternating current voltage is applied to the cylindrical electrode tube, resulting in formation of a glow discharge plasma, and accordingly the outer surface of the tube can be selectively treated.

In the surface treatment by the atmospheric pressure glow discharge plasma method of the present invention, it is of paramount importance to apply an alternating current voltage on the surface to be treated. The frequency of the applied alternating voltage for the alternating current is not limited to a specific frequency, and can be determined as required, depending on such various factors such as the type of plasma treatment method selected including plasma CVD, plasma grafting and plasma polymerization; control modes for rates of treatment or film-forming; types of plasma-polymerizable monomers to be introduced and types of materials to be treated. However, a frequency less than 1 GHz is preferred for treatment of plastic substrates according to the present invention.

In the above surface treatment of the invention, it is sufficient only to replace air present in the atmospheric pressure glow discharge plasma region with a mixture of a glow discharge-stabilizing gas and a treating gas, but it is preferred to continuously introduce the above mixture gas after the gas replacement has been completed in the plasma region.

A mixing ratio of the glow discharge-stabilizing gas to the treating gas in the gas mixture is preferably 100% /5 to 0,001%. The glow discharge-stabilizing gas described above includes inert gases such as helium, argon, neon, krypton, xenon and nitrogen; a mixture of helium and other inert gases such as a mixture of helium and argon; and further a mixture of argon and ketones and a mixture of argon and methane. Preferable gases include, but are not limited to, helium, argon, a mixture of argon and helium, and a mixture of argon and ketones.

Any polymeric materials can be used as a material to be treated for surface reforming. Such materials include polyethylene (PE), polypropylene (PP), polyethylene terephthalate, polyurethane, polyimide, poly(vinyl chloride), poly(vinylidene chloride), polyfluorovinylidene, polycarbonate, polyacetal, polyester, silicone resin, polytetrafluoroethylene, acrylic resin, poly(acrylic acid), poly(acryl amide), polymethylmethacylate, poly(vinyl acetate), poly(vinyl alcohol), polyacrylonitrile, polystyrene, polysulfone, poly(ethylene oxide), poly(ether etherketone), poly(ether sulfone) and the like, but are not limited to these compounds.

Further, copolymer materials that can be used in accordance with this invention include ethylene/vinyl alcohol copolymer, ethylene/vinyl acetate copolymer, ethylene/tetrafluoroethylene copolymer, hexafluoropropylene/tetrafluoroethylene copolymer and ABS resin.

The treating gas described above includes various polymerizable monomers such as ethylene, propylene, isobutene, vinyl chloride, vinylidene chloride, tetrafluoroethylene, hexafluoropropylene, trifluoroethylene and the like, but are not limited to these compounds.

In addition, the treating gas can include those intrinsically non-polymerizable compounds such as saturated hydrocarbons, tetrafluoromethane, monosilane, disilane, ethylene oxide and ammonia under conditions in which these compounds can form graft chains and films on the surface of materials to be treated and can reform on the surface as required when they are introduced to the treating vessel in combination with the glow discharge stabilizing gas.

Those polymerizable monomers that can be coated on the material for subsequent atmospheric pressure glow discharge plasma treatment include acrylic acid; methacrylic acid; alkyl(metha)acrylates such as methyl(metha)acrylate, ethyl(metha)acrylate, n-propyl(metha)acrylate, n-butyl(metha)acrylate, isobutyl(metha)acrylate, t-butyl(metha)acrylate, and 2-ethylhexyl(metha)acrylate; hydroxyalkyl(metha)acrylates such as 2-hydroxyethyl(metha)acrylate, and 2-hydroxypropyl(metha)acrylate; alkylaminoalkyl(metha)acrylates such as methylaminoethyl(metha)acrylate, ethylaminoethyl(metha)acrylate, dimethyl aminoethyl(metha)acrylate, and diethylaminoethyl(metha)acrylate; alkoxyalkyl(metha)acrylates such as methoxyethyl(metha)acrylate and ethoxyethyl(metha)acrylate; acrylamide; methacrylamide; alkyl(metha)acrylamides such as N-methyl(metha)acrylamide, N-ethyl(metha)acrylamide, and i-propyl(metha)acrylamide; dialkyl(metha)acrylamides such as N-dimethyl(metha)acrylamide, N-diethyl(metha)acrylamide, and isopropyl(metha)acrylamide; acrylonitrile; methacrylonitrile; acryloylmorpholine; acryloylpyrrolidine; acryloylpiperidine; vinyl polymerizable monomers such as vinylpyrrolidone, vinylproline, vinylsilane, vinylpyridine and vinylquinoline, but are not limited to these compounds.

In a preferred atmospheric pressure glow discharge plasma treatment of this invention, hydrophilic monomers can be used as the above treating gas or as the above polymerizable monomer that can be coated on the surface of materials to be treated because they make that surface hydrophilic and facilitate formation of a hydrogel layer as well.

Since this invention makes outer surface of a PE tube hydrophilic, printing properties, for example, are expected to be improved, and the hydrogel surface thus obtained is resistant to adherence of blood clots and blood corpuscles and hence is known to display anti-thrombotic properties. Therefore, this can be used to produce a material having excellent anti-thrombotic properties. Further, use of biocompatible monomers such as acryloyl morpholine and hydroxyethylmethacrylate as the above hydrophilic monomers can convert the material to be treated to a medical material having excellent biocompatibility.

Use of tetrafluoroethylene gas for the treating gas provides a pseudo film of polytetrafluoroethylene (PTFE) on the surface of the substrate material to be treated. This film can make the surface hydrophobic. The PTFE, which is inert on its surface, is good in lubricity and stable to chemicals, making a useful plastic material. On the other hand, this PTEF is poor in flexibility among other physical properties and thus has limited uses.

Hence, use of soft PVC and soft polyurethane as the plastic substrate to be treated can overcome the above-mentioned disadvantage. Formation of PTFE films on the soft PVC can increase lubricity and chemical stability present on the surface. On the other hand, properties such as flexibility as a bulk material are maintained as the same as the soft PVC used as a base material.

Furthermore, it has been known that PTFE can hardly absorb blood components such as blood platelet, and hence is matchless in anti-thrombotic properties. The PTFE therefore can provide an anti-thrombotic surface on the treated material, and a medical material can be produced which has both bulk properties of soft PVC and surface properties of PTFE, for example.

BRIEF DESCRIPTION OF THE DRAWINGS

FIG. 3 is a schematic perspective view of another embodiment of an electrode used in the reactor system of the present invention.

FIG. 4 is a schematic perspective view of another embodiment of an electrode used in the reactor system of the present invention.

FIG. 11 is a schematic perspective view of an additional embodiment of the electrode of the present invention.

FIG. 12 is a schematic cross-sectional view of an embodiment of an apparatus for producing anti-thrombotic medical materials of the present invention.

DESCRIPTION OF THE PREFERRED EMBODIMENTS

Figure 1:
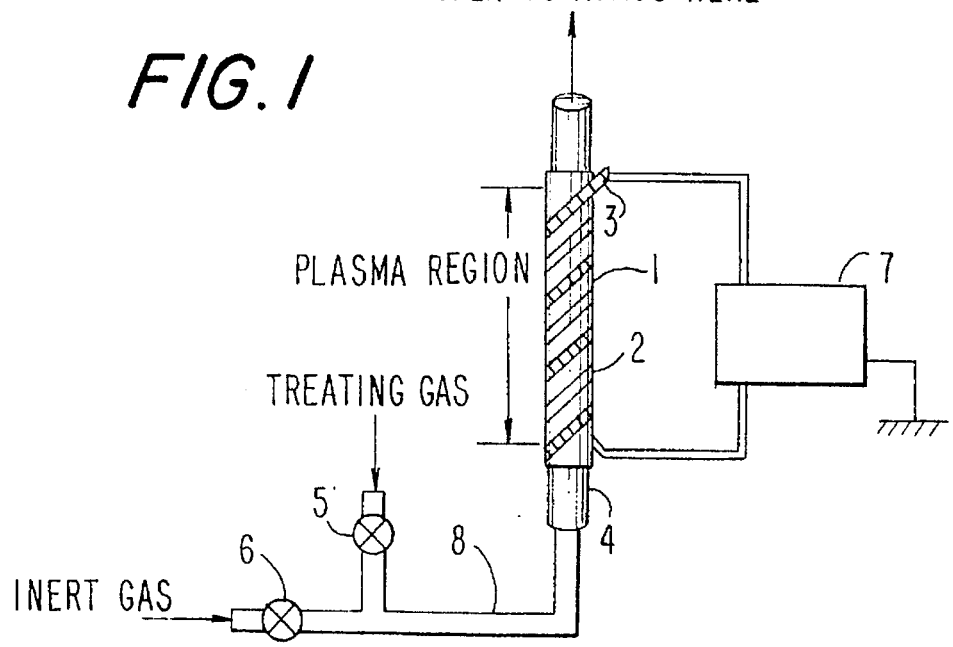
FIG. 1 is a schematic drawing for an embodiment of a reactor system of the invention for treatment of the inner surface of a plastic tube.

The atmospheric pressure glow discharge plasma treatment of the present invention can be conducted, for example, using a treatment apparatus having an electrode body 1 as shown in FIG. 1.

Figure 2:
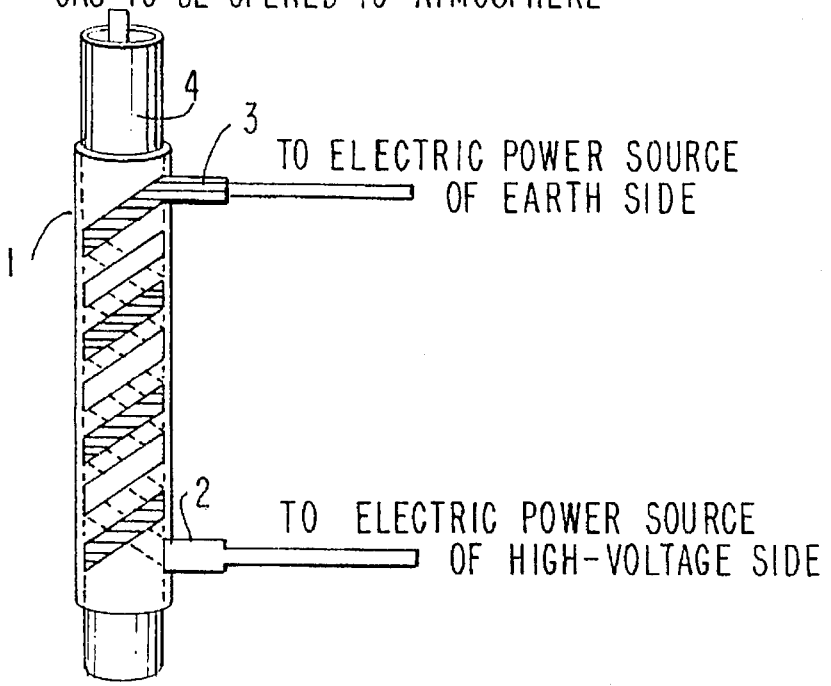
FIG. 2 is an enlarged perspective view of a dual helical electrode of the present invention.

The electrode body 1, as shown in an enlarged view of FIG. 2, comprises a high-voltage side electrode 2 and a ground-side electrode 3, both of which are made of electrically conductive materials and which, are helically wound around a cylindrical insulator that is made of plastic material, ceramic material and the like. The electrodes can be attached to the inner surface of the insulator or imbedded in the insulator.

The method is performed as follows. First, insert a substrate to be treated 4, e.g. a tube, through the electrode body 1 and connect the lower end of the substrate with a gas feed line 8 while the upper end is open to the atmosphere. Secondly, open mass-flow control valves 5 and 6 located in the gas feed line 8 to continuously introduce a mixture of a glow discharge-stabilizing gas and a treating gas into the substrate 4, and then apply an alternating current voltage to the electrode body 1 at a pressure near to atmospheric pressure to form a glow discharge plasma region for surface treatment.

The atmospheric pressure glow discharge plasma is excited at the electrode body 1 itself and inside the substrate 4 only so that the inner surface of the substrate material 4 can be treated with plasma while the outer surface retains the original physical properties since no treatment is received.

Alternatively, an apparatus can be used which only exposes the outer surface to the plasma. According to the present invention, therefore, selective treatment by atmospheric pressure glow discharge plasma can be conducted by various embodiments of an apparatus to treat different portions of the surface of the substrate according to the invention and by subsequent control of the operation of these embodiments.

As to the structure of the electrode body, in addition to the above electrode body 1 comprising one high voltage side electrode and the other ground-side electrode strips wound helically as shown in FIG. 2, other electrode bodies as shown in FIGS. 3 and 4 may be used for treatment with an atmospheric pressure glow discharge plasma. It should be understood that the present invention is not limited to the electrode bodies as shown herein.

Referring to the cylindrical electrode body 1 of FIG. 2, each electrode strip of the high-voltage side electrode 2 and the ground-side electrode 3 is helically wound around the inside of the body so as to form together a double helix. The width of the electrode strip is preferably not larger than one-third of the diameter of the cylindrical electrode body 1. The distance between the high-voltage side electrode and the ground-side electrode is preferably 10 to 300% of the electrode width.

A plurality of high-voltage side electrodes 12 and ground-side electrodes 13 can be alternatively disposed or arranged in the cylindrical electrode body 11 as shown in FIG. 3 for treating an elongated substrate material.

A high-voltage side electrode 22 and a ground-side electrode 23 are arranged opposed to each other and extend in the axial direction along the inner surface of the body in a cylindrical electrode body 21 shown in FIG. 4. The distance between the high-voltage side electrode 22 and the ground-side electrode 23 is preferably 10 to 300% of the electrode width and should vary together with its width as the inner diameter of the cylindrical electrode body 21 changes.

EXAMPLE 1

A soft PVC tube having an inner diameter of 6.5 mm and an outer diameter of 8.4 mm was washed and dried for use as a test sample. It was then fed into the electrode body shown in FIG. 1. A gas mixture of helium and tetrafluoroethylene (TFE) was continuously fed into the tube 8 and an alternating current voltage with a frequency of 10 KHz was applied across the electrodes 2 and 3 at a pressure near to atmospheric pressure for 10 minutes in a plasma treatment. Then, measurements of the angle of contact of water on the surface treated with the plasma were made. Formation of the film on the surface was also confirmed by surface analysis using ATR-IR.

Then, a tube sample was coated with acrylamide (AAm) dissolved in methanol and was dried for subsequent treatment. Helium was continuously introduced into the tube sample and an alternating current voltage with a frequency of 10 KHz was applied across the electrodes at a pressure near to atmospheric pressure for a plasma treatment which lasted 10 minutes. Then, in a similar manner, measurements of ATR-IR and the angle of contact were conducted.

Results of Example 1

Table 1 shows the results of measurements for the angle of contact of water on the treated surface. When compared with those of untreated PVC, TFE showed an increase while AAm showed a decrease in the contact angle, this confirmed that the atmospheric pressure glow discharge plasma treatment can make the surface either hydrophobic or hydrophilic depending on the added gas (TFE or AAm).

TABLE 1

| Angle of Contact of Water on Surfaces Plasma treated at Atmospheric Pressure | | | |
| --- | --- | --- | --- |
| Treating Gas | TFE | AAm | PVC (untreated) |
| Angle of Contact | 113.3 | 64.7 | 88.3 |

Figure 5:
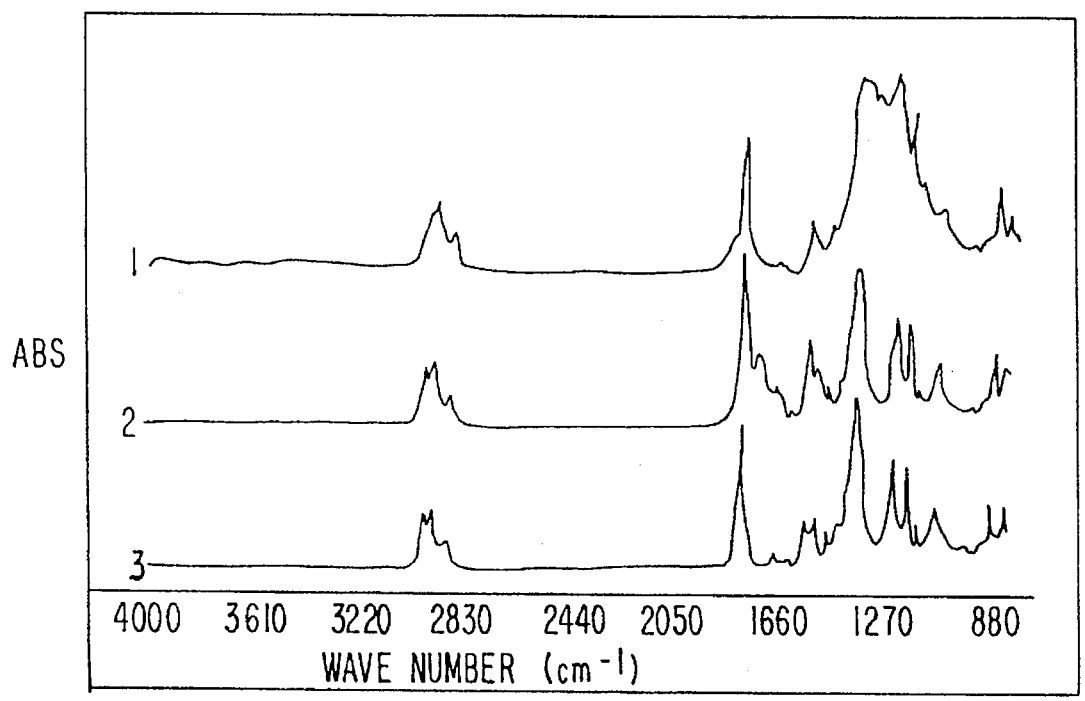
FIG. 5 is a graphical illustration showing ATR-IR spectrometer measurements for the tubes treated with the atmospheric pressure glow discharge plasma process obtained by the method of Example 1 of the present invention.

Results obtained with ATR-IR measurement are shown in FIG. 5. When spectrum (1) for TFE treated PVC is compared with spectrum (3) for untreated PVC, a new absorption band has been found in a region of 1250–1100 cm−1 range which corresponds to a C—F bond. This result confirmed formation of a TFE film on the PVC surface. When spectrum (2) for AAm-treated PVC is compared with spectrum (3) for untreated PVC, there is an increase in absorption strength at 1700 cm−1 which corresponds to a C=O bond, and a new absorption band has been found around 1600 cm−1 which corresponds to a C—N bond, this confirming formation of an AAm film on PVC surface. Thus, it has been confirmed that the atmospheric pressure glow discharge plasma treatment can create a film on the surface of a PVC substrate and can make the surface either hydrophilic or hydrophobic depending on its film properties.

EXAMPLE 2

A soft PVC tube having an inner diameter of 4.7 mm and an outer diameter of 6.8 mm was used as a specimen, which was then subjected to a plasma treatment for 15 minutes in the same manner as in Example 1. Then, the sample thus treated was cut to a length of 15 mm, and then in half lengthwise. This sample was immersed in rabbit fresh platelet plasma (PRP) and incubated at 37° C. for 30 minutes.

Then, this was immobilized using glutaraldehyde, and after dehydration a sample was prepared for an electron microscopic according to the standard procedure. A scanning electron microscope (SEM) was used to observe and evaluate adherence and coagulation of platelets on the treated surface.

Results of Example 2

Figure 6:
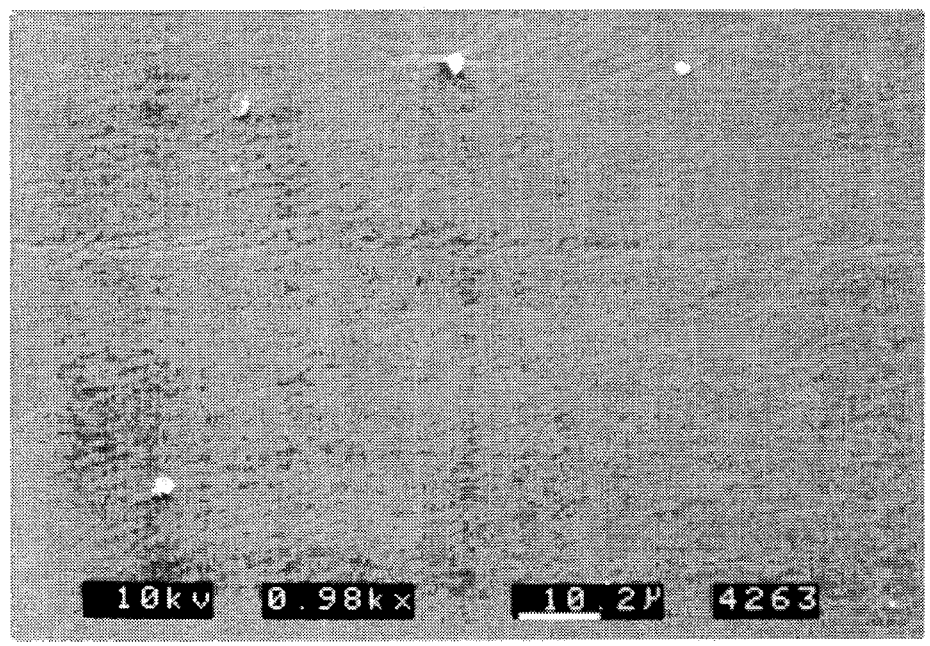
FIG. 6 is a SEM photo (×1000) taken after a TFE treated PVC tube was contacted with rabbit fresh PRP.
Figure 7:
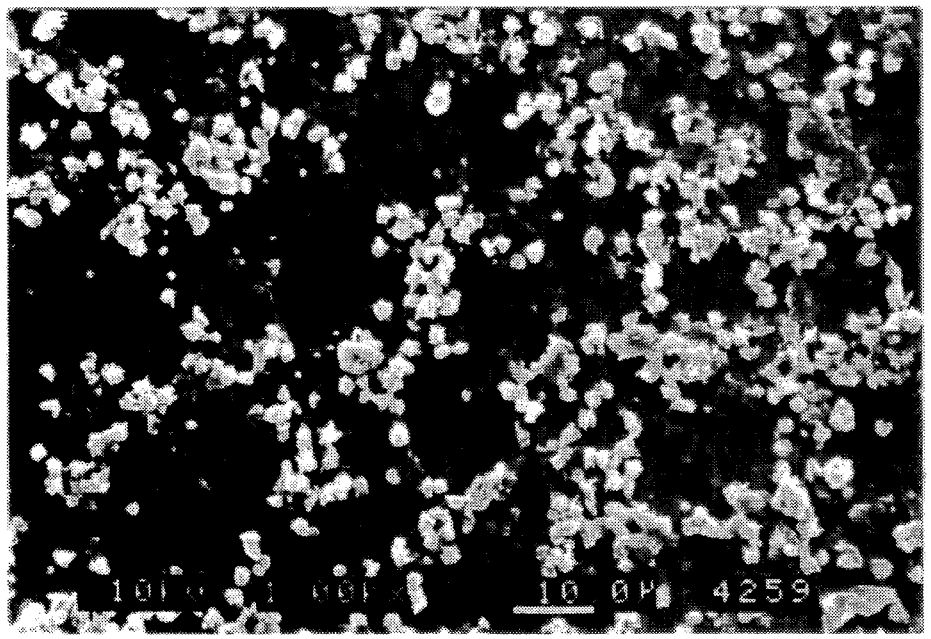
FIG. 7 is a SEM photo (×1000) taken after a untreated PVC tube (control) was contacted with rabbit fresh PRP.

As shown in FIG. 6, neither adherence nor coagulation of platelet were observed in the plasma treated sample, while adherence of a significant number of platelets was observed in the control untreated specimen as shown in FIG. 7. Thus, it has been confirmed that the treatment of the invention provides a medical material having improved anti-thrombotic properties.

This material has been found to be advantageous for a medical material which contacts with blood and which is used in catheters and blood circuits. This material has various uses in different medical fields.

Figure 8:
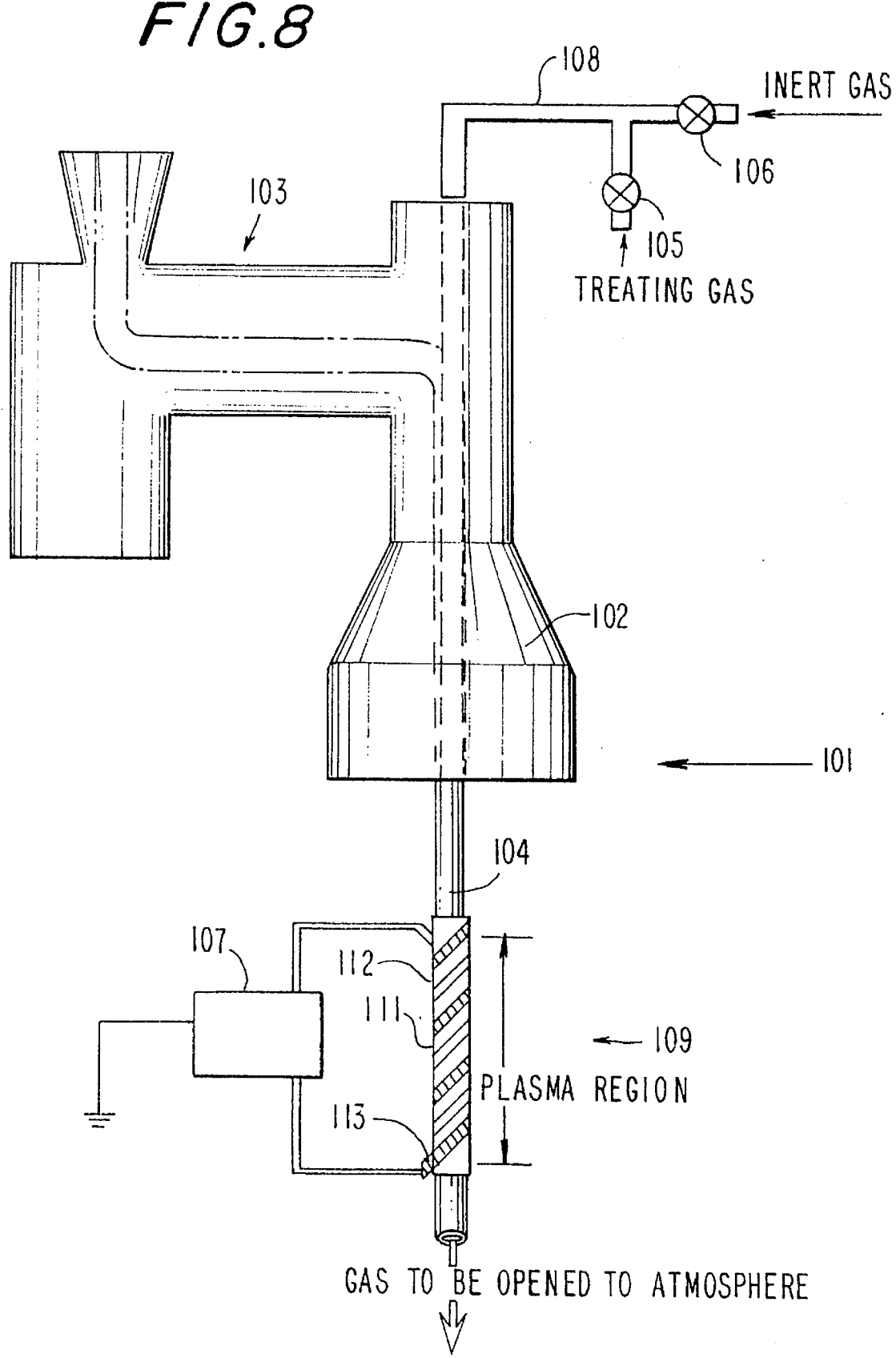
FIG. 8 is a schematic drawing of an embodiment of an apparatus for producing anti-thrombotic medical materials of the present invention.

FIG. 8 illustrates a schematic representation of an apparatus 101 for producing anti-thrombotic medical materials. The apparatus 101 consists of an extruder 103 equipped with a metal mold 102 and a plasma treatment unit 109 located downstream of the metal mold 102. A gas feed line 108 is provided passing from the rear of the metal mold 102 through the inside of the metal mold 102.

The plasma treatment unit 109 consists of the electrode body 111 with a high-voltage side electrode 112 and a ground-side electrode 113 that are alternately and helically wound around a cylinder; and a high frequency electric power source 107 connected with the above electrodes. In the manufacturing apparatus 101, use of insulating materials for the gas feed line 108 can reduce an increase in temperature of the gas mixtures including the treating gas.

A tube 104 is extruded from the extruder 103 through the metal mold 102 to the plasma treatment unit 109. The tube 104 to be treated is open to the atmosphere at its lower end. Then, mass-flow control valves 105 and 106 located in the gas feed line 108 are opened to continuously supply a mixture of a glow discharge-stabilizing gas and a treating gas into said tube 104, and then the alternating current voltage from the high-frequency electric power source 107 is applied to the electrode body 111 at a pressure near to atmospheric pressure to form a glow discharge plasma region for surface treatment.

The atmospheric pressure glow discharge plasma is excited at the electrode 111 itself and inside of the tube 104 only, so that the inner surface of the tube 104 can be treated while the outer surface is unaffected, maintaining the original physical properties. Alternatively, an arrangement can be made with which only the outer surface can be treated by plasma. According to the present invention therefore, selective treatment with an atmospheric pressure glow discharge plasma can be conducted by varying the features of the apparatus and subsequent methods of operation.

Figure 10:
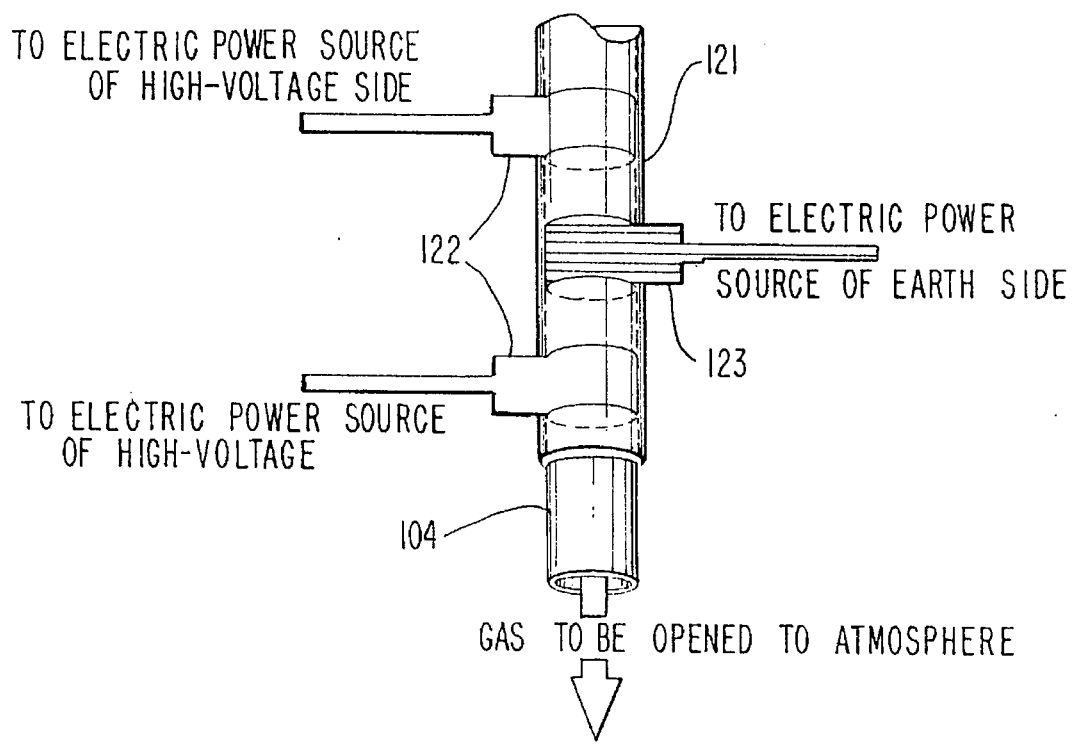
FIG. 10 is a schematic perspective view of another embodiment of the electrode of the present invention.

As to the structure of the electrode body 111 in the plasma treatment unit 109, in addition to the above electrode body 111 in which one high-voltage side electrode 112 and the other ground-side electrode 113 strips are wound helically around a cylindrical plastic or ceramic insulator, other types of electrode bodies as shown in FIGS. 10 and 11 may be used for treatment by atmospheric pressure glow discharge plasma.

Figure 9:
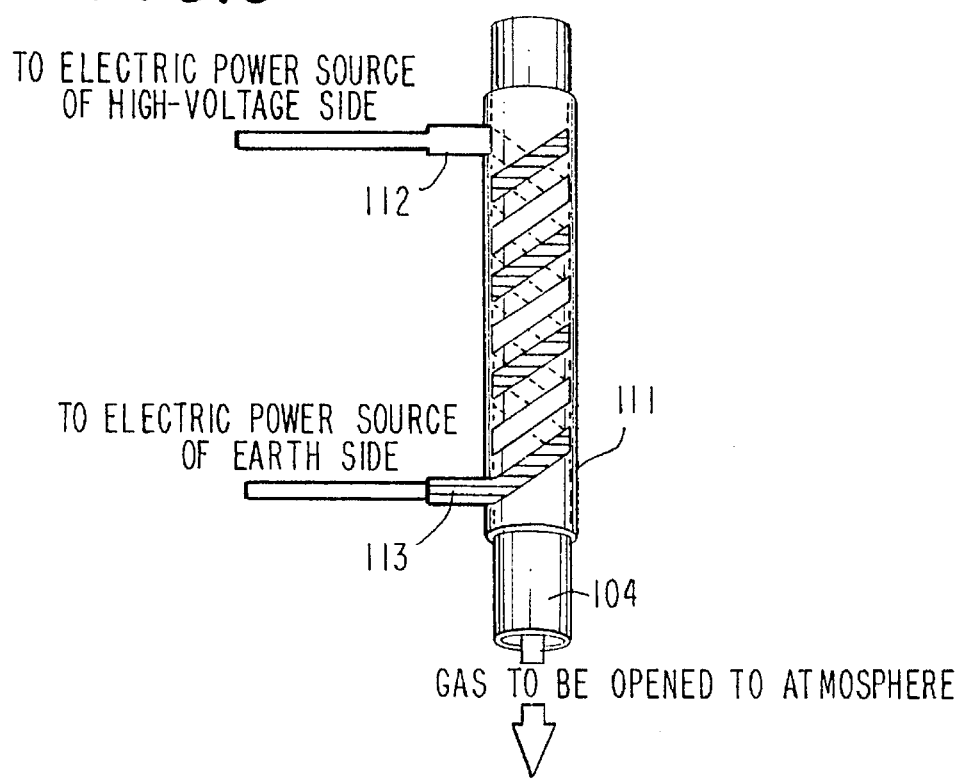
FIG. 9 is an enlarged schematic perspective view of the dual helical electrode shown in FIG. 8.

Referring to the cylindrical electrode body 111 of FIG. 9, each electrode strip of the high-voltage side electrode 112 and the ground-side electrode 113 is dual-helically wound around the inside of the body. The width of the electrode strip is preferably not larger than one-third of the diameter of the cylindrical electrode body 111. The distance between the high-voltage side electrode 112 and the ground-side electrode 113 is preferably 10 to 300% of the electrode width. The cylindrical electrode body 121 shown in FIG. 10 is obtained by alternately disposing a plurality of electrode strips of both high-voltage side electrode 122 and ground-side electrode 123 around a cylinder, and is suitable for treating an elongated substrate.

In a cylindrical electrode body 131 of FIG. 11, high-voltage side electrode 132 and ground-side electrode 133 are arranged opposite to each other and extending in the axial direction along the inner surface of the body. The distance between the high-voltage side electrode 132 and the ground-side electrode 133 is preferably 10 to 300% of the electrode width, and should be changed together with its width as the inner diameter of the cylindrical electrode body 131 changes.

FIG. 12 is a schematic representation of an apparatus 140 for producing anti-thrombotic medical materials, which comprises an insulator housing 145 made of glass and the like and an insulator tube 146 also made of glass and the like that is inserted in the insulator housing 145.

Around the outer circumference of the insulator tube 146, a high-voltage side electrode 142 and a ground-side electrode 143 are wound helically, and a lubricant 149, for example, a fluoride resin is coated on the inner surface. Insulating oil, for example, a silicone oil is filled in a space between the insulator tube 146 and the insulating housing 145, and can be cooled or heated as it is circulated through a heat exchanger 148 via a circulation pipe 150. The heat exchanger system permits the control of temperature, and temperature adjustment can be made by suppressing temperature increases in the electrodes 142 and 143 as well as setting the treating temperature by heating.

Other electrode arrangements besides the dual-helical arrangement shown in FIG. 9 can be used in the producing apparatus 140 as shown in FIGS. 10 and 11.

The tube 104, which is open to the atmosphere at its lower end, is conveyed through the inside of the insulator tube 146. Then, as in the case of the apparatus 101 of FIG. 8, a mixture of the glow discharge-stabilizing gas and the treating gas is continuously fed into the tube 104 while the tube 104 being conveyed through the interior of the insulator tube 146. Then an alternating current voltage from the high frequency electric power source (not shown) is applied across the above electrodes 142 and 143 at a pressure near to atmospheric pressure to form a glow discharge plasma region for surface treatment.

In the producing apparatus 140, since the surface of the electrodes does not contact the atmosphere, undesirable plane discharge is suppressed so that the life of the electrodes can be extended. In addition, it becomes possible to apply a higher voltage to the electrodes for attaining a higher treatment efficiency.

Instead of the tubular material 104, the treated material can be a sheet of material.

In the plasma treatment apparatus 101 and 140, the time during which the tube travels through the electrodes, i.e. the residence time, or the treating time can be determined by adjusting the length of the electrodes and the transfer rate of the tube.

In the producing apparatus 101 of FIG. 8, an apparatus 140 of FIG. 12 can be used instead of the plasma treating unit 109. An additional mechanism that permits rotation of the tube or electrodes can provide more uniform treatment during which the substrate tube to be treated is conveyed. More uniform treatments can be made by providing rotation to the tube or electrodes without conveying the tube at all.

Figure 13:
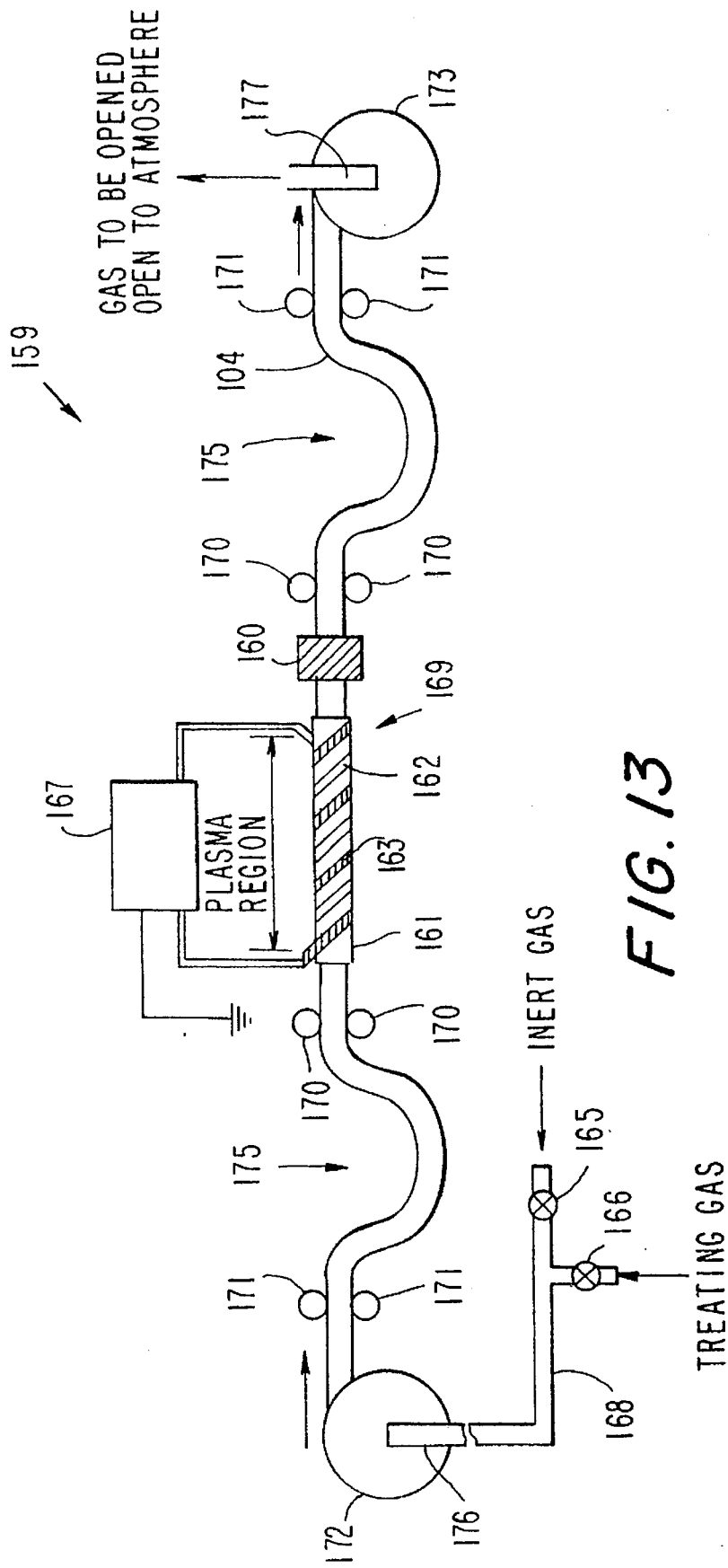
FIG. 13 is a schematic view of an embodiment of an apparatus for manufacturing plastic tubes of the present invention.

FIG. 13 illustrates a schematic representation of an apparatus 159 for producing plastic tubes in which the tubes are continuously treated while being rotated and conveyed. A tube drum 172 is located on the inlet side of a plasma treatment unit 169 while a tube take-up reel drum 173 is located on the outlet side of the unit 169. Two sets of tube driving rollers 170 are disposed on the respective downstream and upstream sides of the plasma treatment unit 169. A tube rotating device 160 is located between the downstream tube driving rollers 170 and the plasma treatment unit 169. The rollers 171 are tube guide rollers.

Figure 14:
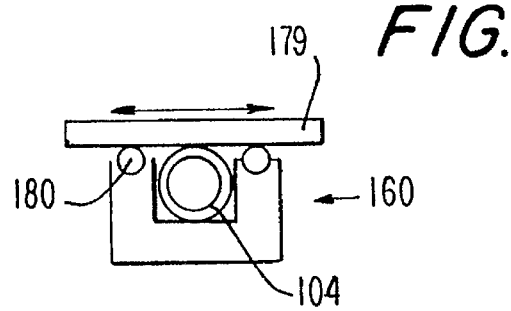
FIG. 14 is a schematic cross-sectional view of a tube rotating device arranged in the apparatus shown in FIG. 13.

A gas supply mechanism 176 is provided for the tube drum 172 to supply gas to the inside of the tube 104, while a gas-vent mechanism 177 is provided for the tube take-up real drum 173a to allow gas having passed through the tube to be released to the atmosphere. The tube rotation unit 160 has a rotating or twisting mechanism that provides a rotation or twist motion of the tube 104 by moving a slide plate 179 horizontally along rollers 180 as shown in FIG. 14.

In the case that a material to be treated is a soft plastic tube 104, for example, the tube 104 is wound around the tube drum 172 and a slackened tube zone 175 that allows rotation or twist of the tube 104 is formed along the tube.

The tube 104 is continuously passed through the plasma treatment unit 169 by the roller 170 while it is being rotated or twisted by the tube rotation unit 160. Then, the mass-flow control valves 165 and 166 located in the gas feed line 168 are opened to continuously feed a gas mixture of the glow discharge-stabilizing gas and the treating gas into the inside of the tube 104, and the alternating current voltage is applied to the electrode body from a high-frequency electric power source 167 at a pressure near to atmospheric pressure to form a glow discharge plasma region for surface treatment.

After plasma treatment, the tube 104 is transferred to the take-up reel drum 173. On the way to that drum, the tube 104 is subjected to rotation or twist action by the tube rotation unit 160. The slackened zone 175 located before the take-up reel drum 173 but after the rotation unit 160 can prevent the tube 104 from twisting during take-up. As to the shape of the electrode body 161 that constitutes the plasma treatment unit 169, for example, such shapes as shown in FIGS. 9, 10, and 11 can be used, and, instead of the plasma unit 169, a plasma treatment apparatus 140 of FIG. 12 can also be used.

EXAMPLE 3

A soft PVC tube having an inner diameter of 6.5 mm and an outer diameter of 8.4 mm was washed and dried to prepare a test specimen, which was then conveyed to the apparatus 140 of FIG. 12. Gas mixtures of 1) helium and hexafluoropropylene (HFP) and 2) helium and ammonia ($NH_3$) were continuously introduced into the tube and a 3 kV alternating current voltage having a frequency of 10 KHz was applied across the electrodes at a pressure near to atmospheric pressure for a residence time of 10 minutes to perform a plasma treatment. For each gas mixture, samples of 2 meters in length were prepared. Further, 3) a PVC tube with a length of 2 meters was coated with vinyl pyrolidone (VPy) and dried. Then, helium gas was continuously fed into the tube and a 3 kV alternating current voltage having a frequency of 10 KHz was applied across the electrodes at a pressure near to atmospheric pressure for 10 minutes' residence time plasma treatment. Afterwards, measurement of the angle of contact of water on the surface of each sample was made for each sample.

Results of Example 3

Table 2 shows results of the measurement of the angle of contact. When compared with those of untreated PVC, TFE indicated an increase in the angle of contact while $NH_3$ and VPy showed a decrease in the angle of contact, this confirming that the atmospheric pressure glow discharge plasma treatment can make the surface either hydrophobic or hydrophilic depending on the added gas (TFE, $NH_3$ and VPy).

TABLE 2

Change in Angle of Contact after Glow Discharge Plasma Treatment at Atmospheric Pressure

| Treating Gas | Angle of Contact,°[1] |
|---|---|
| TFE | 108.3 |
| NH3 | 47.1 |
| VPy | 39.5 |
| PVC(untreated) | 88.3 |

[1]Average of 20 random measurements

EXAMPLE 4

A soft PVC tube having an inner diameter of 4.7 mm and an outer diameter of 6.5 mm was washed and dried for preparation as test specimen, and was then passed through the apparatus 140 of FIG. 12. A gas mixture of 1) helium and tetrafluoroethylene (TFE) was continuously fed into the tube and a 3 kV alternating current voltage having a frequency of 10 KHz was applied across the electrodes at a pressure near to atmospheric pressure for a 10 minutes' residence time plasma treatment. A samples of 2 meters in length was prepared. Afterwards, in order to confirm formation of film on the surface, a FT IR-ATR method was used. Surface FT IR-ATR analysis was conducted at 5 points along the tube with an interval of 50 cm from the initial point of treatment.

Results of Example 4

Figure 15:
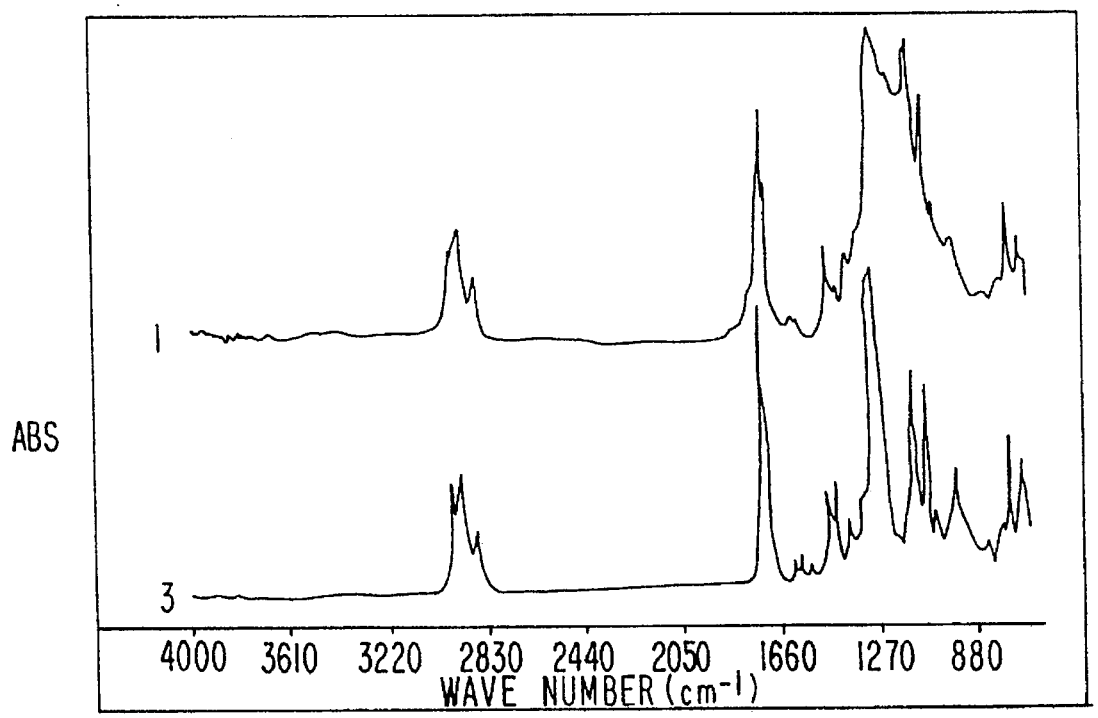
FIG. 15 is a graphical illustration showing ATR-IR spectrometer measurement results obtained at the one meter point of the tubes treated with the atmospheric pressure glow discharge plasma process according to the example 4.

Results obtained by FT IR-ATR are shown in FIG. 15. When spectrum (1) for TFE-treated PVC is compared with spectrum (3) for untreated PVC, a new absorption band was found located in spectrum (1) in the 1250–1100 cm$^{-1}$ region which is characteristic of a C—F bond. The confirmed that a TFE film has formed on the PVC surface of the treated PVC and that the surface was made hydrophobic by the atmospheric pressure glow discharge plasma treatment.

The FT IR-ATR spectrum for polytetraflourethylene in fact shows two peaks in the vicinity of 1205 and 1140 cm−1 that correspond to the C—F bond. On the other hand, spectrum (1) is the same as spectrum (3) except in the region of 1205 and 1140 cm−1.

With a constant distance from the surface where the infrared rays strike, relative strength of absorption in the region of 1250–1100 cm−1 varies with the TFE film thickness.

Therefore, the ratio of the absorption strength at 1205 cm−1 corresponding to the C—F bond to an absorption strength at a peak attributed to the bulk material provides a measure of the relative amount of the coated film.

Based on the knowledge described above, an FT IR-ATR analysis was conducted of the surface of the 2-meter tube that was continuously treated in the plasma treatment. Altogether, 5 points were selected for analysis with an interval of 50 cm from the initial point of treatment. Formation of film on surface was thus confirmed by obtaining ratios of absorption strength at 1205 cm−1 to that at 1722 cm−1. Here, the band at 1722 cm−1 corresponds to a C═O bond attributed to a plasticizer contained in soft PVC bulk material. The ratios of absorbancy are shown in Table 3.

TABLE 3

1205 cm–1/1722 cm–1 Absorption Ratios of at
Various Points along Continuously Plasma Treated Tube

|  | (1)1205 cm–1 | (2)1722 cm–1 | (1)/(2) |
| --- | --- | --- | --- |
| Initial Point | 0.173 | 0.191 | 0.92 |
| 50 cm Point | 0.161 | 0.189 | 0.86 |
| 1 m Point | 0.186 | 0.179 | 1.06 |
| 1.5 m Point | 0.179 | 0.186 | 0.95 |
| 2 m Point | 0.183 | 0.184 | 1.00 |

It is clearly shown from the data in Table 3 that the (1)/(2) ratios, which were obtained at arbitrary points along the continuously treated tube, are virtually the same, and this agreement of the ratios indicates that uniform coating was attained for the entire surface. According to the present invention, therefore, uniform films on the inner surface of the treated tube can be obtained by continuous coating.

EXAMPLE 5

A soft PVC tube having an inner diameter of 4.7 mm and an outer diameter of 6.8 mm was used as a test specimen, and was then subjected to 15 minutes' plasma treatment in the same manner as in Example 3. Then, the test specimen thus treated was cut to a length of 15 mm, and then in half lengthwise. One of the resulting halves was immersed in rabbit fresh platelet plasma (PRP) and incubated at 37° C. for 30 minutes.

Then, it was immobilized using glutaraldehyde, and after dehydration a sample of the PRP treated test specimen was prepared for an electron microscopic view according to standard procedure. A scanning electron microscope (SEM) was used to observe and evaluate adherence and coagulation of plasma platelets on the treated surface of the sample.

Results of Example 5

Figure 16:
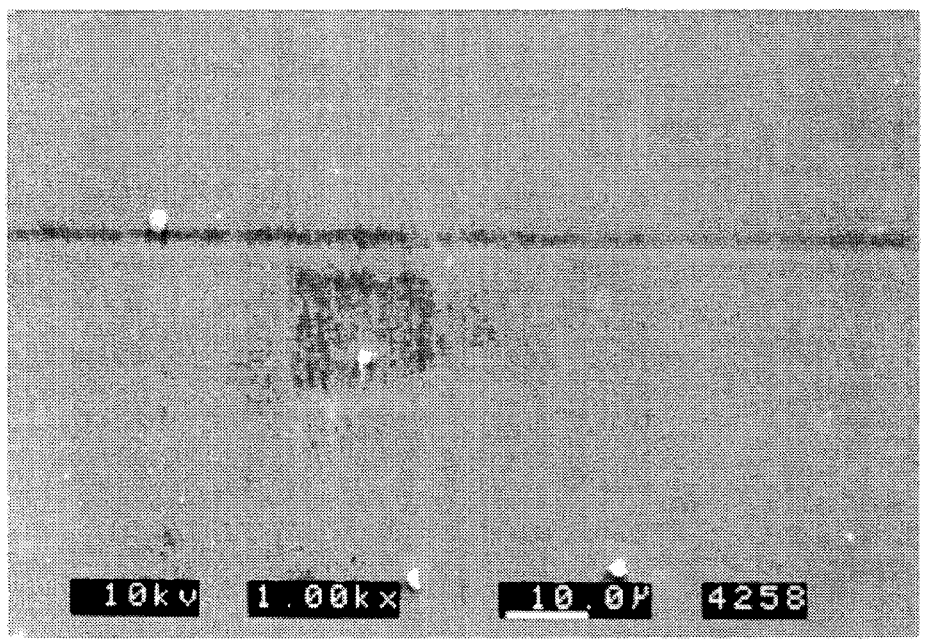
FIG. 16 is a SEM photo (×1000) taken after a TFE treated PVC tube was contacted with rabbit fresh PRP.
Figure 17:
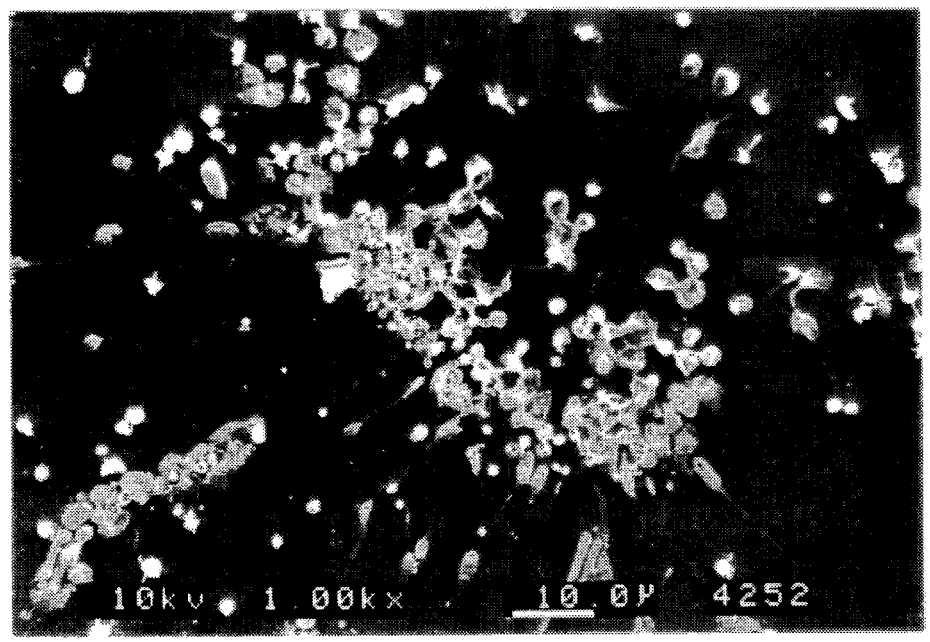
FIG. 17 is a SEM photo (×1000) taken after a untreated PVC tube (control) was contacted with rabbit fresh PRP.

As shown in FIG. 16, no adherence or coagulation of platelets were observed in the plasma-treated sample while adherence of significant amounts of platelets were observed in a control untreated specimen as shown in FIG. 17. Thus, it was confirmed that the treated tube of the invention had improved anti-thrombotic properties.

The resultant material thus has been found to be advantageous for such medical materials as catheters and blood circuits that contact with blood. Various uses for these medical materials can be found in different medical appliances.

Materials for the high-voltage side electrode and the ground-side electrode used in the present invention can include electrically conductive metal plates such as copper, iron, gold, stainless steel and the like; and copper- or gold-coated plastic or ceramic plates. The same materials of construction can be used for electrodes 212, 213, 222, 223, 232, 233, 242, and 243 that will be described hereinafter.

Figure 18:
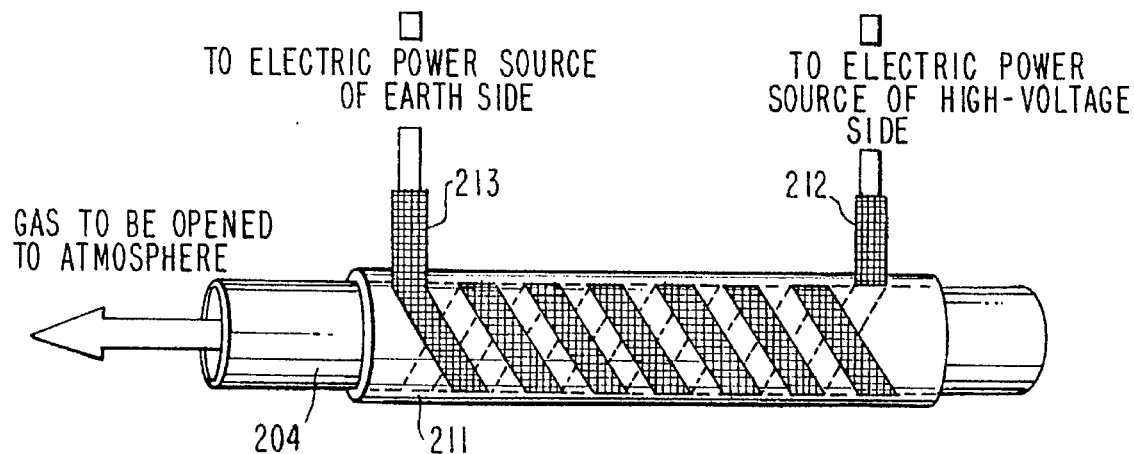
FIG. 18 is a schematic perspective view of another embodiment of the electrode of the present invention.

As an electrode body 211 in the plasma treatment unit shown in FIG. 18, electrically conductive meshed materials can be used as a high-voltage side electrode 212 and a ground-side electrode 213. Further, as an electrode body 221 in the plasma treatment unit shown in FIG. 19, electrically conductive materials that have been coated with a lubricant 226 on the inner surface and that have been covered with a metal-mesh sheet on the outer surface can be used as a high-voltage side electrode 222 and a ground-side electrode 223 that are alternatively disposed.

A metal mesh, which is either directly formed as the electrode body 211 or used as a cover as shown in the electrode body 221 in the plasma treatment unit, can improve uniformity of treatment between the electrodes. Inert gases, for example, argon and nitrogen can assist more stable discharge treatment.

Figure 20:
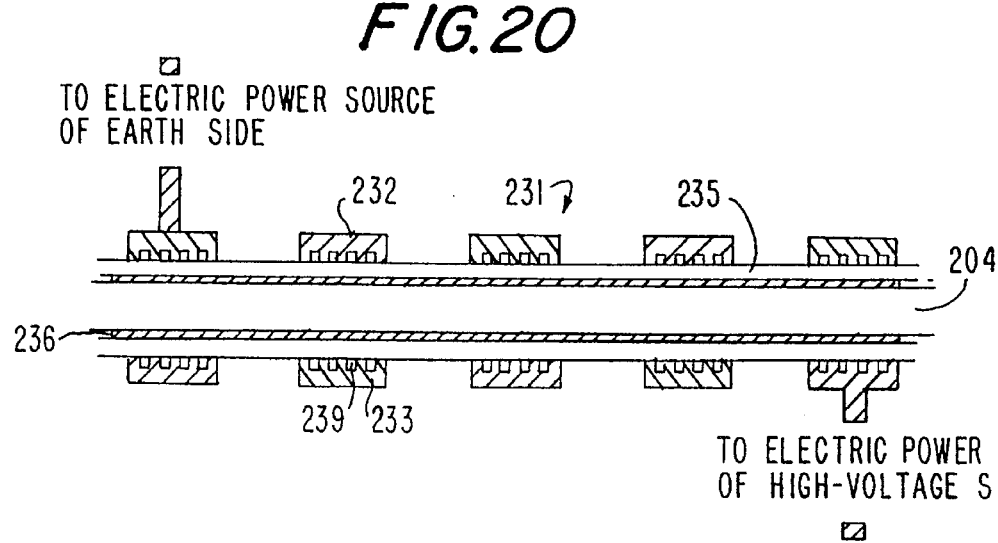
FIG. 20 is a schematic cross-sectional view of an additional embodiment of the electrode of the present invention.

As illustrated in an electrode body 231 in the plasma treatment unit of FIG. 20, uniform discharge can be obtained by forming grooves 239 in the contact surface between the insulator 235 and both the high-voltage side electrode 232 and the ground-side electrode 233.

EXAMPLE 6

A soft PVC tube having an inner diameter of 3.3 mm and an outer diameter of 5.5 mm was washed and dried as a test specimen, and was then put inside a dual-helical type electrode body made of different materials as shown in Table 4. Helium, argon and nitrogen were each used separately as a glow discharge-stabilizing gas, and were each continuously fed into the above tube. An alternating current voltage having a frequency of 20 KHz was applied across the electrodes to produce a glow discharge plasma.

Table 4 shows results of the above-described experiments. The stability of the resulting plasma was determined in the case of Helium and Argon.

Results of Example 6

TABLE 4

Results of Example 6

|  | Materials of Electrode/Gas | Helium | Argon |
| --- | --- | --- | --- |
| 1 | Copper Plate | 0 | X |
| 2 | Copper Mesh | 0 | 0 |
| 3 | Stainless Mesh | 0 | 0 |
| 4 | Copper Plate/Copper Mesh | 0 | 0 |
| 5 | Copper/Stainless Mesh | 0 | 0 |

0: Stable
X: Unstable

EXAMPLE 7

A soft PVC tube having an inner diameter of 6.5 mm and an outer diameter of 8.4 mm was washed and dried as a test specimen, and was then put in the electrode body 211 shown in FIG. 18. A gas mixture of argon and tetrafluoroethylene (TFE) was continuously fed into the tube and an alternating current voltage having a frequency of 20 KHz was applied across the electrodes at a pressure near to atmospheric pressure for a minutes' residence time plasma treatment. In order to attain a good treatment uniformity, the PVC tube 204 was rotated inside the electrode body 211 at three rotations per minute.

Results of Example 7

Figure 21:
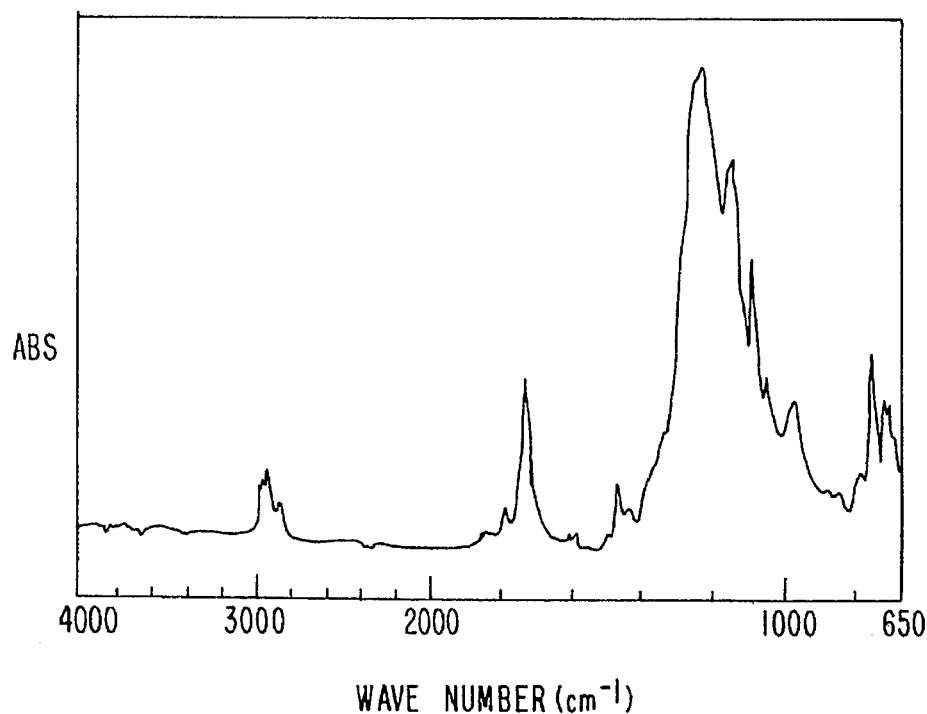
FIG. 21 is a graphical illustration showing ATR-IR measurement results conducted for the tubes treated with the atmospheric pressure glow discharge plasma process according to example 7.

Results obtained by FT IR-ATR are shown in FIG. 21. A new absorption band has been found in a region of 1250–1100 cm$^{-1}$ that corresponds to a C—F bond, this confirming that the TFE film has formed on the PVC surface under argon atmosphere in the same manner as under helium atmosphere.

For example, in electrode bodies 1, 11 and 21 as shown in FIGS. 2, 3, and 4, respectively, both ground-side and high-voltage side electrodes are outside the tube. Alternatively, however, it is possible for either a ground-side electrode 243 or a high-voltage side electrode 242 to be inside the treated tube as illustrated in the electrode body 241 in the plasma treatment unit of FIG. 22.

The electrode body 241 comprises a tubular high-voltage side electrode 242 and a ground-side electrode 243, and the high-voltage side electrode 242 is fixed inside the tube 204 with an electrode-fixing member 246 having gas exhaust pipes 244 for venting a gas mixture that has been introduced. On the other hand, the ground-side electrode 243 is fixed outside an insulating glass tube 245. Alternatively, the ground-side electrode 243 may be fixed inside the tube 204 while the high-voltage side electrode 242 may be outside the insulating glass tube 245 in the electrode body 241.

In the above case, the insulating glass tube 245 also functions as a shape-maintaining support for the tubular high-voltage side electrode 242, for example. Therefore, if the tubular high-voltage side electrode 242 can maintain its tubular shape by itself, then this glass tube is not necessarily used.

However, an electrode plate may be heated by applying an alternating current voltage on the high voltage side electrode 242. Then, if a glass insulating tube 245 is used, it prevents the evolved heat from transmitting directly to the treated material, permitting stable treatment even on a less-heat-resistant material.

Figure 19:
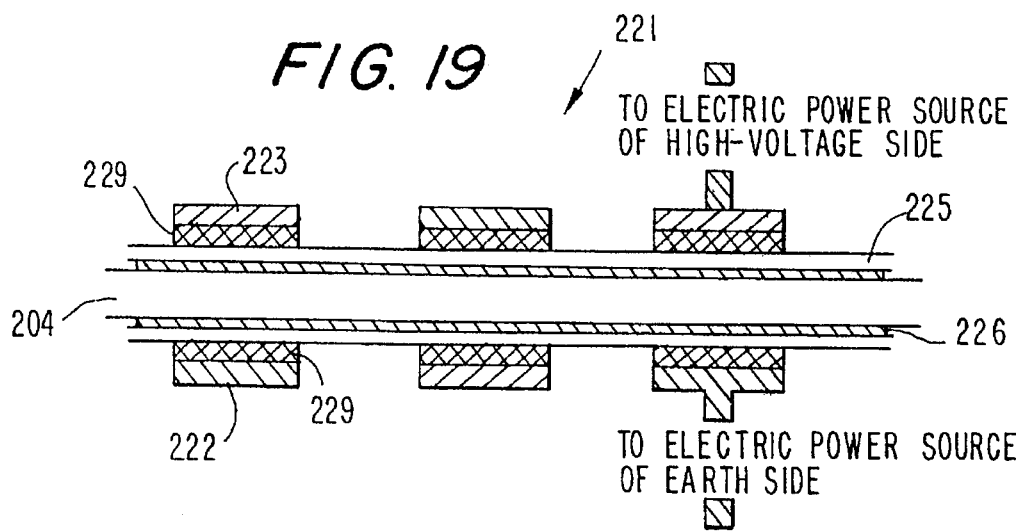
FIG. 19 is a schematic cross-sectional view of another embodiment of the electrode of the present invention.

This insulating effect due to glass is not limited to the electrode body 241, but the same effect is also expected in insulating glass tubes 146, 225, and 235 used in electrode bodies 140, 221, and 231 of the plasma treatment unit of FIGS. 12, 19, and 20, respectively. This effect produced by the insulating glass tubes 146 is not necessarily obtained only by glass. Any insulating materials having low thermal conductivity can be used that include plastics and ceramics.

EXAMPLE 8

Figure 22:
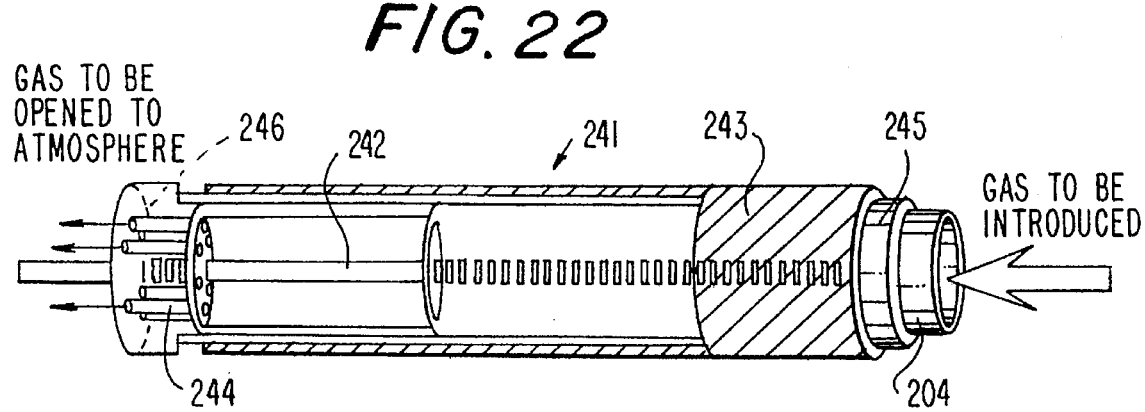
FIG. 22 is a schematic perspective view of another embodiment of the electrode of the present invention.

A soft PVC tube having an inner diameter of 12.5 mm and an outer diameter of 17.5 mm was washed and dried as a test specimen, and was then set in the electrode body 241 of FIG. 22. A gas mixture of helium and hexafluoropropylene (HFP) was continuously introduced into the tube 204 and an alternating current voltage having a frequency of 20 KHz was applied across the electrodes at a pressure near to atmospheric pressure for a 10 minutes' residence time plasma treatment. In order to attain a good uniform treatment, the PVC tube 204 was rotated inside a glass tube 245 in the electrode body 241 at three rotations per minute. Although a larger size tube was used in this example, a smaller size tube may be treated as well.

Results of Example 8

Figure 23:
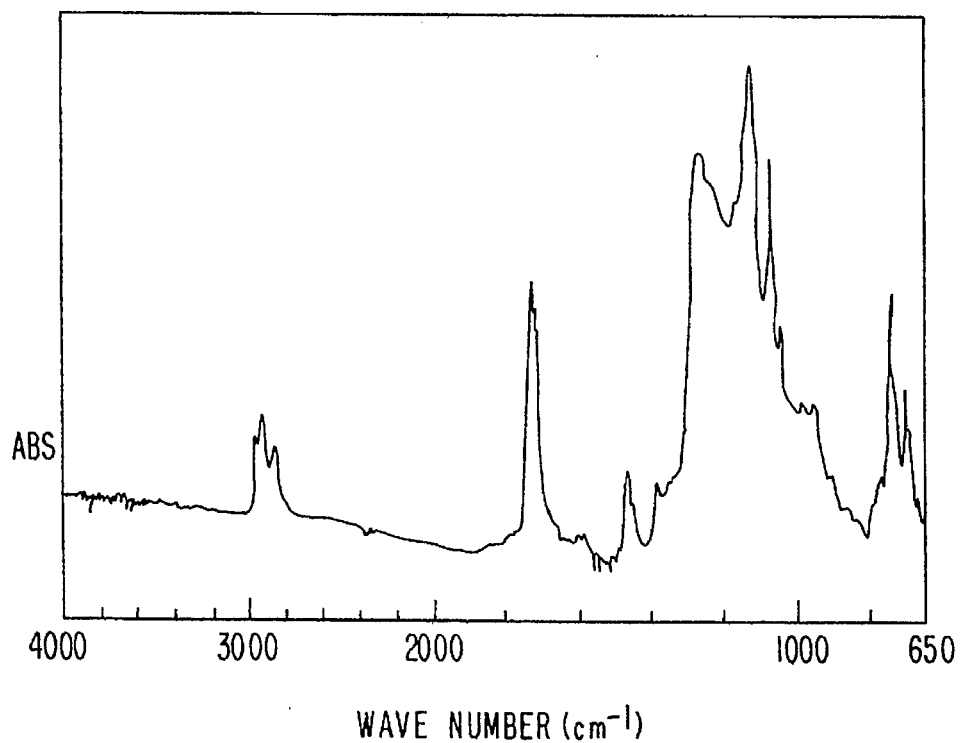
FIG. 23 is a graphical illustration showing ATR-IR measurement results conducted for the tubes treated with the atmospheric pressure glow discharge plasma process according to example 8.

Results obtained by ATR-IR are shown in FIG. 23. An absorption band corresponding to a C—F bond has been found in a region of 1250–1100 cm−1, this confirming formation of film on PVC surface.

Electrode bodies 211, 221, 231, and 241 as shown in FIGS. 18, 19, 20, and 22, respectively, can also be applied to the aforementioned manufacturing apparatus 101, 140, and 159.

Figure 24:
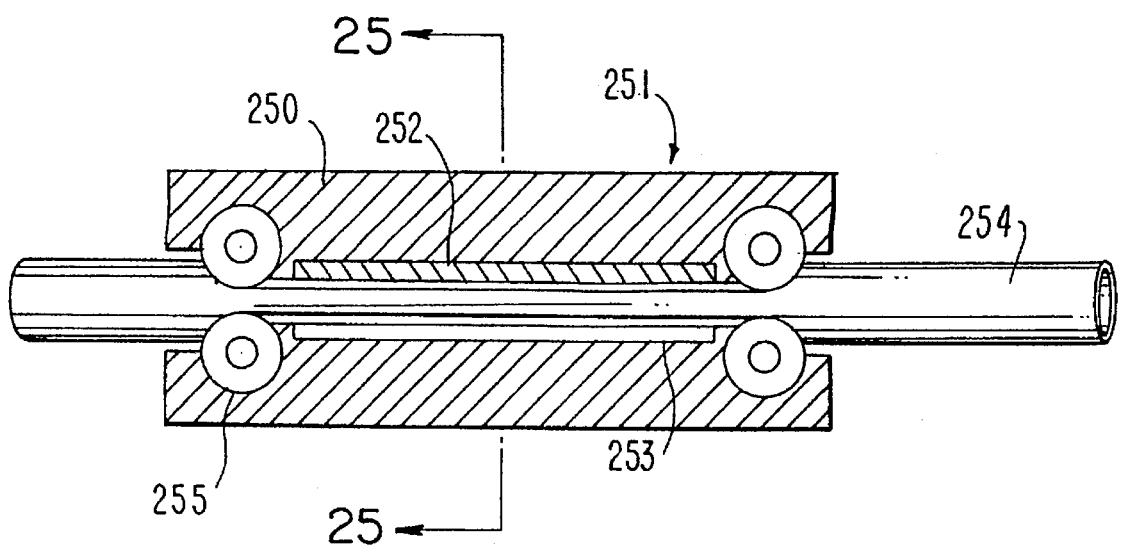
FIG. 24 is a schematic longitudinal cross-sectional view through another embodiment of the plasma treatment apparatus of the present invention.
Figure 25:
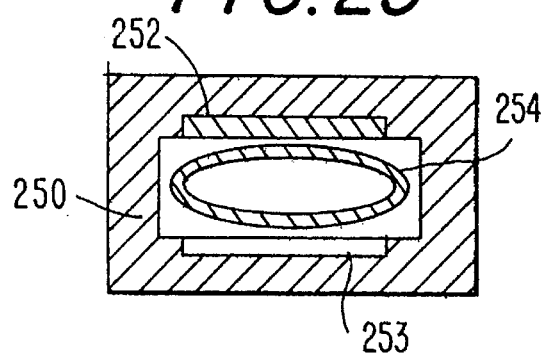
FIG. 25 is a transverse cross-sectional view taken along the section line A—A of FIG. 24.

FIG. 24 shows an electrode body 251 in a plasma treatment unit where a tubular material 254 to be treated is being flattened as it is treated. FIG. 25 shows a cross-sectional view taken on a line A—A of FIG. 24.

As to the plasma treating unit 251, for example, a high-voltage side electrode plate 252 and a ground-side electrode plate 253 are facing each other in such a manner that the material to be treated 254 is between both the plates or entirely surrounded by both the plates inside a rectangle housing 250. For example, cylindrical rollers 255 are located at the inlet and outlet side of the plasma treating unit 251, and these rollers can convey the treated material while they flatten it.

Flattening the treated tube material allows a distance between the high-voltage side electrode 242 and ground-side electrode 243 to be comparatively small so as to obtain a small electrode discharge gap.

Hence, use of the plasma treating apparatus 251 of this example can increase plasma discharge efficiency for larger diameter flexible synthetic resin tubes. The larger diameter the tube, the more advantageous.

The plasma treating apparatus 251 can replace the apparatus 101 of FIG. 8 and the apparatus 140 of FIG. 12.

Further, in the plasma treating apparatus 251, the high voltage side electrode 252 and ground-side electrode 253 can be replaced by high voltage side electrodes 2, 12, 22, 112, 122, 132, 142, 162, 212, 222, 232, and 242 and ground-side electrodes 3, 13, 23, 113, 123, 133, 143, 163, 213, 223, 233, and 243 of FIGS. 2, 3, 4, 9, 10, 11, 12, 13, 18, 19, 20, and 22, respectively.

In order to treat the outer surface of the tube material, in the case of electrode bodies of FIGS. 12, 19, 20, and 22, for example, where the electrodes are on insulator tubes 225, 235, 245, for example, a glow discharge-stabilizing and a treating gas are introduced into a narrow space between the tube material and the insulator tube, and the alternating current voltage is then applied for developing glow discharge between the tube material and the insulator tube.

Alternatively, in order to treat the outer surface of the tube material, it is also possible that, after the tube surface has been coated with monomers, a glow discharge-stabilizing gas is introduced into a narrow space between the tube material and the insulator tube, and the alternating current voltage is then applied for developing glow discharge between the tube material and the insulator tube.

Further, the electrode bodies 221, 231, and 241 as shown in FIGS. 19, 20, and 22 can be used for the apparatus 140 of FIG. 12. In other words, instead of electrodes 142 and 143, they can be inside the insulating housing 145, and outside the insulator tube 146.

As described above, according to the present invention, without employing vacuum systems for a plasma region, glow discharge plasma region can be formed by applying the alternating current voltage under an atmosphere of a glow discharge-stabilizing gas at a pressure neighboring to atmospheric pressure. According to this method, treatments including plasma initiation polymerization, plasma CVD, plasma graft polymerization and the like can be made. In addition, according to this atmospheric pressure glow discharge plasma treatment, medical materials with anti-thrombotic properties can be produced.

Another object of this invention is to provide novel medical materials and methods for producing the same, where use of treating gas comprising monomers is made to produce surface films excelling in blood compatibility such as anti-thrombosis.

According to the invention, compared with conventional low-temperature glow discharge plasma method, no units or facilities for vacuum systems are necessary, thus the treatment is less costly. Further, it is possible to provide antithrombotic properties by selective surface treatment such as graft and film formation. Film formation on PVC surface can prevent a plasticizer from leaving the bulk PVC material.

Use of anti-thrombotic medical materials obtained according to the present invention can easily produce blood circuits, catheters, blood bags which are excellent in antithrombotic property. In summary, the present invention can be applied to manufacture medical apparatus that are excellent in blood compatibility such as antithrombotic properties.

While the invention has been illustrated and described as embodied in a medical material having anti-thrombotic properties and method of making same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Method of making medical materials comprising the steps of:
   a) exposing at least one surface of a material to a gas mixture comprising a glow discharge-stabilizing gas and a treating gas, said gas mixture having a pressure substantially equal to atmospheric pressure; and
   b) applying an alternating current voltage to the material during said exposing step a) to perform a plasma glow discharge treatment of said at least one surface of said material wherein said treatment produces an anti-thrombotic film on said at least one surface of said material.

2. Method as defined in claim 1, wherein said material is a plastic tube having an interior surface and two ends, one of said two ends being open to a surrounding atmosphere, and said at least one surface of the material consists of said interior surface of said plastic tube, and said exposing comprises feeding said gas mixture into another of said two ends of said plastic tube remote from said end open to said surrounding atmosphere.

3. Method as defined in claim 2, further comprising providing a tubular electrode body, inserting said plastic tube through said tubular electrode body and applying said alternating current voltage to said tubular electrode body to create a plasma region in said gas mixture adjacent said interior surface of said tube to perform said plasma glow discharge treatment.

4. Method as defined in claim 3, further comprising flattening said plastic tube and wherein said applying of said alternating current voltage to said tubular electrode body is performed during said flattening of said plastic tube.

5. Method as defined in claim 1, wherein said material to be treated is a plastic tube having an outer surface and said at least one surface of said material to be treated is said outer surface, and further comprising providing a tubular electrode body through which said plastic tube fits so as to provide a narrow space between said plastic tube and said tubular electrode body and feeding said gas mixture of said glow discharge-stabilizing gas and said treating gas into said narrow space between the plastic tube and the tubular electrode body.

6. Method as defined in claim 1, wherein a ratio of said glow discharge-stabilizing gas to said treating gas ranges from 100/5 to 100/0.001.

7. The method as defined in claim 1, wherein said glow discharge-stabilizing gas is at least one member selected from the group consisting of helium, argon, neon, krypton, xenon, nitrogen, ketones, and methane and said treating gas is at least one gas compound selected from the group consisting of polymerizable organic monomers, saturated hydrocarbons, tetrafluoromethane, monosilanes, disilanes, ethylene oxide and ammonia.

8. A method of treating tubular medical materials with an atmospheric pressure glow discharge plasma, said method comprising the steps of:
   a) extruding a plastic tube having an interior surface;
   b) passing said plastic tube through a tubular electrode body;
   c) feeding a gas mixture comprising a glow discharge-stabilizing gas and a treating gas through said plastic tube during the extruding step a) and the passing step b); and
   d) applying an alternating current voltage to said tubular electrode body at a pressure substantially equal to atmospheric pressure to create a plasma region in said plastic tube to perform a glow discharge plasma treatment of said interior surface to form a treated plastic tube having anti-thrombotic properties.

9. A method of treating tubular medical materials with an atmospheric pressure glow discharge plasma, said method comprising the steps of:
   a) providing a tube to be treated, said tube having an interior surface and two ends, one of said two ends being open to a surrounding atmosphere;
   b) conveying said tube through an electrode body and twisting said tube during said conveying;
   c) feeding a gas mixture of a glow discharge-stabilizing gas and a treating gas into another of said two ends of said tube during said conveying of said tube through said electrode body wherein said gas mixture flows through said tube; and
   d) applying an alternate current voltage to said electrode body to create a plasma region in said gas mixture in said tube at a pressure substantially equal to atmospheric pressure during said feeding step c) to perform a glow discharge plasma treatment of said interior surface of said tube to from a treated tube having anti-thrombotic properties.

10. A method of making medical materials comprising the steps of applying an alternating current voltage to a material in the presence of a glow discharge-stabilizing gas to form a plasma region in said glow discharge-stabilizing gas at atmospheric pressure to form an active ligand on at least one surface of the material and then feeding a treating gas into said plasma region, to perform a plasma glow discharge treatment to said at least one surface thereof to form a medical material having anti-thrombotic properties.

11. A method of producing medical materials, said method comprising the steps of coating a material with a polymerizable monomer, applying an alternating current voltage to said coated material in the presence of a glow discharge stabilizing gas at a pressure substantially equal atmospheric pressure to form a plasma region in said gas at a pressure substantially equal to atmospheric pressure to perform a plasma glow discharge treatment of the coated material to form a medical material having an anti-thrombotic property.

12. A method as defined in claim 11, wherein said polymerizable monomer is a hydrophilic monomer.

* * * * *